United States Patent [19]

Becker et al.

[11] Patent Number: 4,517,013

[45] Date of Patent: May 14, 1985

[54] CYCLOHEXANE-1,3-DIONE DERIVATIVES AND THEIR USE FOR CONTROLLING UNDESIRABLE PLANT GROWTH

[75] Inventors: Rainer Becker, Bad Durkheim; Dieter Jahn, Edingen-Neckarhausen; Michael Keil, Ludwigshafen; Walter Himmele, Walldorf; Bruno Wuerzer, Otterstadt, all of Fed. Rep. of Germany

[73] Assignee: BASF Aktiengesellschaft, Fed. Rep. of Germany

[21] Appl. No.: 515,898

[22] Filed: Jul. 21, 1983

[51] Int. Cl.³ .................... A01N 31/04; A01N 33/24; C07C 149/14
[52] U.S. Cl. .......................... 71/98; 71/103; 71/105; 71/106; 71/121; 560/125; 260/464; 564/256; 564/300
[58] Field of Search .................. 564/256, 300; 71/98, 71/103, 105, 106, 121; 560/125, 126; 260/465.5 R, 484

[56] References Cited

FOREIGN PATENT DOCUMENTS 1589003 5/1981 United Kingdom .

*Primary Examiner*—Natalie Trousof
*Assistant Examiner*—L. Hendriksen
*Attorney, Agent, or Firm*—Keil & Weinkauf

[57] ABSTRACT

Cyclohexane-1,3-dione derivatives of the formula

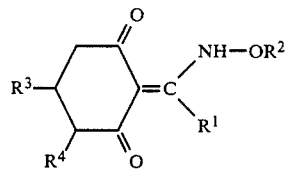

where $R^1$ is $C_1$–$C_4$-alkyl, $R^2$ is $C_1$–$C_5$-alkyl, unsubstituted or halogen-substituted $C_2$–$C_5$-alkenyl or $C_2$–$C_5$-alkynyl, $R^3$ is $C_1$–$C_{10}$-alkyl, which contains 2, 3 or 4 of the hetero-atoms O and/or S and/or the groups —SO— and/or —SO$_2$— in any desired position and $R^4$ is hydrogen, cyano, methyl or —COOR$^5$, where $R^5$ is $C_1$–$C_5$-alkyl, and salts of these compounds are used for controlling undesirable plant growth.

7 Claims, No Drawings

CYCLOHEXANE-1,3-DIONE DERIVATIVES AND THEIR USE FOR CONTROLLING UNDESIRABLE PLANT GROWTH

The present invention relates to cyclohexane-1,3-dione derivatives, herbicides containing these compounds as active ingredients, and their use for controlling undesirable plant growth.

German Laid-Open Application DOS No. 2,822,304 discloses that cyclohexane-1,3-dione derivatives can be used for selectively controlling undesirable grasses.

We have found that cyclohexane-1,3-dione derivatives of the formula

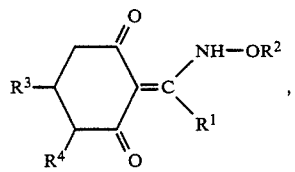

where $R^1$ is $C_1$-$C_4$-alkyl, $R^2$ is $C_1$-$C_5$-alkyl, unsubstituted or halogen-substituted $C_2$-$C_5$-alkenyl or $C_2$-$C_5$-alkynyl, $R^3$ is $C_1$-$C_{10}$-alkyl, which contains 2, 3 or 4 of the hetero-atoms O and/or S and/or the groups —SO— and/or —SO$_2$— in any desired position and $R^4$ is hydrogen, cyano, methyl or —COOR$^5$, where $R^5$ is $C_1$-$C_5$-alkyl, and salts of these compounds, have a herbicidal action on grasses and do not damage broad-leaved crops and monocotyledonous crops which do not belong to the grass family (Gramineae), but on the other hand, surprisingly, are selective in cereal varieties which do belong to the Gramineae.

The compounds of the formula I can occur in several tautomeric forms, all of which are encompassed by the patent claim:

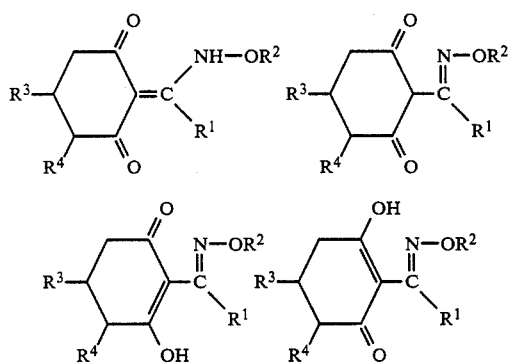

$R^1$ in formula I is straight-chain or branched $C_1$-$C_4$-alkyl, such as methyl, ethyl, n-propyl, i-propyl or n-butyl; $R^2$ is straight-chain or branched $C_1$-$C_5$-alkyl, unsubstituted or halogen-substituted $C_2$-$C_5$-alkenyl or $C_2$-$C_5$-alkynyl, such as methyl, ethyl, n-propyl, i-propyl, n-butyl, i-butyl, t-butyl, allyl, 3-chloro-prop-2-enyl, 2-chloro-prop-2-enyl, 2,3,3-trichloroprop-2-enyl, 2,3-dibromo-prop-2-enyl or propargyl; $R^3$ is straight-chain or branched $C_1$-$C_{10}$-alkyl, which contains 2, 3 or 4 of the hetero-atoms O and/or S and/or the groups —SO— and/or —SO$_2$— in any desired position, eg. alkoxyalkoxyalkyl, alkylthioalkylthioalkyl, alkylthioalkoxyalkyl, alkoxyalkylthioalkyl, alkylsulfonylalkylsulfonylalkyl, alkoxyalkylsulfonylalkyl or alkoxyalkylalkylsulfinylalkyl, such as ethoxyethylthiopropyl, ethylthioethylthiopropyl, ethoxyethylthioethyl, ethylthioethylthioethyl, butoxyethoxyethyl, methoxyethoxyethyl, ethoxyethoxyethyl, 2-ethoxyethylsulfinyl-2-methyl-ethyl or 2-ethoxyethylsulfonyl-2-methyl-ethyl.

$R^4$ is hydrogen, cyano or methyl, or alkoxycarbonyl of the formula —COOR$^5$, where $R^5$ is straight-chain or branched $C_1$-$C_5$-alkyl, such as methyl, ethyl, i-propyl, n-butyl or n-pentyl.

Compounds of the formula I where $R^3$ is alkylthioalkylthioalkyl or alkoxyalkoxyalkyl, each of 3 to 10, in particular 3 to 6, carbon atoms, and $R^4$ is hydrogen are preferred.

Examples of suitable salts of the compounds of the formula I are the alkali metal salts, especially the potassium or sodium salts, alkaline earth metal salts, especially the calcium, magnesium or barium salts, and the manganese, copper, zinc and iron salts.

The compounds of the formula I can be obtained by reacting a compound of the formula

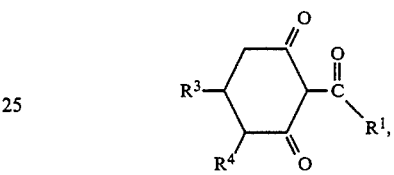

where $R^1$, $R^3$ and $R^4$ have the above meanings, with a hydroxylamine derivative $R^2O$—$NH_3Y$, where $R^2$ has the above meanings and Y is an anion.

The reaction is advantageously carried out in a heterogeneous phase system in an inert diluent at from 0° to 80° C. or from 0° C. to the boiling point of the reaction mixture, in the presence of a base, for example a carbonate, bicarbonate, acetate, alcoholate, hydroxide or oxide of an alkali metal or alkaline earth metal, especially of sodium, potassium, magnesium or calcium. Organic bases, such as pyridine or a tertiary amine, can also be used.

The reaction proceeds particularly well in a pH range from 2 to 8, especially from 4.5 to 5.5. The pH range is advantageously established by addition of an acetate, eg. an alkali metal acetate, especially sodium or potassium acetate or a mixture of the two. From 0.5 to 2 moles of alkali metal acetate are added, for example, per mole of ammonium compound of the formula $R^2O$—$NH_3Y$.

Examples of suitable solvents are dimethylsulfoxide, alcohols, such as methanol, ethanol and isopropanol, benzene, hydrocarbons or chlorohydrocarbons, such as chloroform, dichloroethane, hexane and cyclohexane, esters, such as ethyl acetate, and ethers, such as dioxane and tetrahydrofuran.

The reaction is over after a few hours and the reaction product can then be isolated by concentration of the mixture, addition of water, extraction with a nonpolar solvent, eg. methylene chloride, and distillation of the solvent under reduced pressure.

The compounds of the formula I can also be obtained by reacting a compound of the formula II with a hydroxylamine of the formula $R^2O$—$NH_2$, where $R^2$ has the above meanings, in an inert diluent at from 0° C. to 80° C., especially from 15° to 70° C. Where relevant, an aqueous solution of the hydroxylamine can be used.

Examples of suitable solvents for this reaction are alcohols, such as methanol, ethanol, isopropanol and cyclohexanol, hydrocarbons or chlorohydrocarbons, such as hexane, cyclohexane, methylene chloride, toluene and dichloroethane, esters, such as ethyl acetate, nitriles, such as acetonitrile, and cyclic ethers, such as tetrahydrofuran.

The compounds of the formula I are also obtained by reacting a compound of the formula II with hydroxylamine to give the oxime and alkylating this oxime with a suitable alkylating agent in accordance with the following equation:

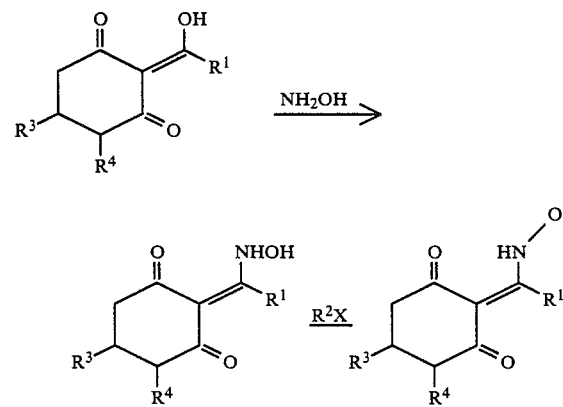

Alkali metal salts of the compounds of the formula I can be obtained by treating these compounds with sodium hydroxide or potassium hydroxide in aqueous solution or in an organic solvent, eg. methanol, ethanol or acetone. Sodium alcoholates and potassium alcoholates can also be used as the bases.

The other metal salts, eg. the manganese, copper, zinc, iron, calcium, magnesium and barium salts, can be prepared from the sodium salts by reaction with a corresponding metal chloride in aqueous solution.

The compounds of the formula II can be prepared from cyclohexane-1,3-diones of the formula III, which can also exist in the tautomeric forms IIIa and IIIb

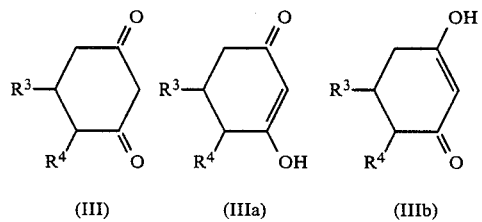

(III)     (IIIa)     (IIIb)

in a conventional manner (Tetrahedron Letters, 29, (1975) (2491).

The derivatives of the formula II can also be prepared by O-acylation of a cyclohexane-1,3-dione of the formula III with subsequent rearrangement under acid catalysis (ALCL$_3$) in accordance with Synthesis (1978) page 925, or basic catalysis (pyridine derivatives) in accordance with Japanese Preliminary Published Application No. 79/063,052.

Compounds of the formula III can be obtained from aldehydes of the formula $R^3$—CH=O in a conventional manner, for example by aldol condensation with acetone and subsequent cyclization with a malonate as described in Organic Synthesis Coll. Volume II, (1950) page 200. Reaction of an aldehyde of the formula $R^3$—CHO with malonic acid (Org. Reactions, Volume 15, (1967) page 204), esterification of the resulting acid and cyclization with ethyl acetoacetate also gives a compound of the formula III, in a process similar to that described in Chem. Ber. 96 2946, (1963). The aldehydes of the formula $R^3$CHO are accessible by adduct formation of a mercaptan with an unsaturated aldehyde (German Pat. No. 855,704) or by hydroformylation of a corresponding vinyl or allyl ether.

A further possibility for synthesizing the compounds of the formula III is the reaction of a γ-halocrotonic acid derivative with a mercaptan or alcohol and cyclization of the resulting γ-mercaptocrotonate or γ-alkoxycrotonate with ethyl acetoacetate as described above.

In the Example which follows and illustrates the preparation of the cyclohexane-1,3-dione derivatives of the formula I, parts by weight bear the same relation to parts by volume as that of the kilogram to the liter.

EXAMPLE 150 parts by volume of ethanol are dissolved in 12.1 parts by weight of 2-butyryl-4-methoxycarbonyl-5-[2-(2-(ethylthio)-ethylthio)-propyl]-cyclohexane-1,3-dione, and 3.3 parts by weight of allyloxyammonium chloride and 2.9 parts by weight of sodium acetate are added. After the mixture has been stirred at room temperature for 20 hours, it is poured into ice-water and extracted with methylene chloride. After stripping off the methylene chloride, 13.0 g of 2-(1-allyloxyaminobutylidene)-4-methoxycarbonyl-5-(2-ethylthio-ethylthio-n-propyl)-cyclohexane-1,3-dione remain as a yellow oil of $n_D^{22.5}$ 1.5446.

$C_{22}H_{35}NO_5S_2$: Molecular weight=458: calculated: C:57.7, H:7.7, N:3.1, S:14.0; found: C:58.0, H:7.5, N:2.9, S:14.0.

The following compounds, for example, were prepared in a similar manner:

| Compound no. | $R^1$ | $R^2$ | $R^3$ | $R^4$ | $n_D$ (Temp. °C.)/NMR-data |
|---|---|---|---|---|---|
| 1 | n-C$_3$H$_7$ | C$_2$H$_5$ | CH$_2$CH(CH$_3$)SCH$_2$CH$_2$SC$_2$H$_5$ | COOCH$_3$ | 1.5497 (22.5) |
| 2 | n-C$_3$H$_7$ | CH$_2$CH=CH$_2$ | CH$_2$CH(CH$_3$)SCH$_2$CH$_2$SC$_2$H$_5$ | COOCH$_3$ | 1.5446 (22.5) |
| 3 | n-C$_3$H$_7$ | C$_2$H$_5$ | CH$_2$CH(CH$_3$)SCH$_2$CH$_2$SC$_2$H$_5$ | H | 1.5476 (22.5) |
| 6 | n-C$_3$H$_7$ | CH$_2$CCl=CCl$_2$ | CH$_2$CH(CH$_3$)SCH$_2$CH$_2$SC$_2$H$_5$ | H | 1.5638 (22.5) |
| 10 | n-C$_3$H$_7$ | CH$_2$CH=CH$_2$ | CH$_2$CH(CH$_3$)SCH$_2$CH$_2$OC$_2$H$_5$ | H | 1.5252 (20.5) |
| 11 | n-C$_3$H$_7$ | C$_2$H$_5$ | CH$_2$CH(CH$_3$)SCH$_2$CH$_2$OC$_2$H$_5$ | H | 1.5300 (22) |
| 16 | n-C$_3$H$_7$ | C$_2$H$_5$ | CH$_2$CH$_2$OCH$_2$CH$_2$O—n-C$_4$H$_9$ | H | 1.4922 (23) |
| 17 | n-C$_3$H$_7$ | CH$_2$CH=CH$_2$ | CH$_2$CH$_2$OCH$_2$CH$_2$O—n-C$_4$H$_9$ | H | 1.4984 (23) |
| 19 | n-C$_3$H$_7$ | C$_2$H$_5$ | CH$_2$CH$_2$OCH$_2$CH$_2$OCH$_3$ | H | 1.5006 (22) |
| 20 | n-C$_3$H$_7$ | CH$_2$CH=CH$_2$ | CH$_2$CH$_2$OCH$_2$CH$_2$OCH$_3$ | H | 1.5078 (22) |
| 21 | n-C$_3$H$_7$ | CH$_2$CH=CHCl | CH$_2$CH$_2$OCH$_2$CH$_2$OCH$_3$ | H | 1.5192 (21) |
| 22 | n-C$_3$H$_7$ | C$_2$H$_5$ | CH(CH$_3$)OCH$_2$CH$_2$O—n-C$_4$H$_9$ | H | 1.4895 (24) |
| 23 | n-C$_3$H$_7$ | CH$_2$CH=CH$_2$ | CH(CH$_3$)OCH$_2$CH$_2$O—n-C$_4$H$_9$ | H | 1.4956 (24) |
| 27 | n-C$_3$H$_7$ | C$_2$H$_5$ | CH(CH$_3$)(OCH$_2$CH$_2$)$_3$OCH$_3$ | H | 1.4979 (22) |
| 28 | n-C$_3$H$_7$ | CH$_2$CH=CH$_2$ | CH(CH$_3$)(OCH$_2$CH$_2$)$_3$OCH$_3$ | H | 1.4976 (22) |

-continued

| Compound no. | $R^1$ | $R^2$ | $R^3$ | $R^4$ | $n_D$ (Temp. °C.)/NMR-data |
|---|---|---|---|---|---|
| 29 | n-$C_3H_7$ | $CH_2CH=CHCl$ | $CH(CH_3)(OCH_2CH_2)_3OCH_3$ | H | 1.5065 (22) |
| 34 | n-$C_3H_7$ | $C_2H_5$ | $CH(CH_3)(OCH_2CH_2)_2OCH_3$ | H | 1.4951 (22) |
| 35 | n-$C_3H_7$ | $CH_2CH=CH_2$ | $CH(CH_3)(OCH_2CH_2)_2OCH_3$ | H | 1.5009 (22) |
| 44 | n-$C_3H_7$ | n-$C_3H_7$ | $CH_2CH_2OCH_2CH_2OCH_3$ | H | 1.5003 (21) |
| 45 | n-$C_3H_7$ | $CH_2-C\equiv CH$ | $CH_2CH_2OCH_2CH_2OCH_3$ | H | $\delta$ = 3.40 ppm ($OCH_3$) |
|  |  |  |  |  | $\delta$ = 2.50 ppm ($\equiv CH$) |

The following compounds may for example be prepared analogously:

| Compound no. | $R^1$ | $R^2$ | $R^3$ | $R^4$ |
|---|---|---|---|---|
| 4 | n-$C_3H_7$ | $CH_2CH=CH_2$ | $CH_2CH(CH_3)SCH_2CH_2SC_2H_5$ | H |
| 5 | n-$C_3H_7$ | $CH_2CCl=CH_2$ | $CH_2CH(CH_3)SCH_2CH_2SC_2H_5$ | H |
| 7 | n-$C_3H_7$ | $CH_2CH=CHCl$ | $CH_2CH(CH_3)SCH_2CH_2SC_2H_5$ | H |
| 8 | n-$C_3H_7$ | $C_2H_5$ | $CH_2CH(CH_3)SO_2CH_2CH_2SO_2C_2H_5$ | H |
| 9 | n-$C_3H_7$ | $C_2H_5$ | $CH_2CH(CH_3)SCH_2CH_2OC_2H_5$ | $COOCH_3$ |
| 12 | n-$C_3H_7$ | $CH_2CH=CHCl$ | $CH_2CH(CH_3)SCH_2CH_2OC_2H_5$ | H |
| 13 | n-$C_3H_7$ | $CH_2CCl=CHCl$ | $CH_2CH(CH_3)SCH_2CH_2OC_2H_5$ | H |
| 14 | n-$C_3H_7$ | $C_2H_5$ | $CH_2CH(CH_3)SOCH_2CH_2OC_2H_5$ | H |
| 15 | n-$C_3H_7$ | $C_2H_5$ | $CH_2CH(CH_3)SO_2CH_2CH_2OC_2H_5$ | H |
| 18 | n-$C_3H_7$ | $CH_2CH=CHCl$ | $CH_2CH_2OCH_2CH_2O-n-C_4H_9$ | H |
| 24 | n-$C_3H_7$ | $CH_2CH=CHCl$ | $CH(CH_3)OCH_2CH_2O-n-C_4H_9$ | H |
| 25 | n-$C_3H_7$ | $C_2H_5$ | $CH(CH_3)(OCH_2CH_2)_3OCH_3$ | $COOCH_3$ |
| 26 | n-$C_3H_7$ | $CH_2CH=CH_2$ | $CH(CH_3)(OCH_2CH_2)_3OCH_3$ | $COOCH_3$ |
| 30 | $C_2H_5$ | $C_2H_5$ | $CH(CH_3)(OCH_2CH_2)_3OCH_3$ | H |
| 31 | $C_2H_5$ | $CH_2CH=CH_2$ | $CH(CH_3)(OCH_2CH_2)_3OCH_3$ | H |
| 32 | n-$C_3H_7$ | $C_2H_5$ | $CH(CH_3)(OCH_2CH_2)_2OCH_3$ | $COOCH_3$ |
| 33 | n-$C_3H_7$ | $CH_2CH=CH_2$ | $CH(CH_3)(OCH_2CH_2)_2OCH_3$ | $COOCH_3$ |
| 36 | n-$C_3H_7$ | $CH_2CH=CHCl$ | $CH(CH_3)(OCH_2CH_2)_2OCH_3$ | H |
| 37 | n-$C_3H_7$ | $CH_2CCl=CH_2$ | $CH(CH_3)(OCH_2CH_2)_2OCH_3$ | H |
| 38 | n-$C_3H_7$ | $C_2H_5$ | $CH_2CH_2OCH_2CH_2SC_2H_5$ | H |
| 39 | n-$C_3H_7$ | $CH_2CH=CH_2$ | $CH_2CH_2OCH_2CH_2SC_2H_5$ | H |
| 40 | n-$C_3H_7$ | $C_2H_5$ | $CH(CH_3)OCH_2CH_2SC_2H_5$ | H |
| 41 | n-$C_3H_7$ | $CH_2CH=CH_2$ | $CH(CH_3)OCH_2CH_2SC_2H_5$ | H |
| 42 | n-$C_3H_7$ | $C_2H_7$ | $CH_2CH_2OCH_2CH_2OCH_3$ | CN |
| 43 | n-$C_3H_7$ | $C_2H_5$ | $CH_2CH_2OCH_2CH_2OCH_3$ | $CH_3$ |

The compounds of the formula I may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredient according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, isobutanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 16 is mixed with 10 parts by weight of N-methyl-alpha-pyrrolidone. A mixture is obtained which is suitable for application in the form of very fine drops.

II. 10 parts by weight of compound no. 17 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

III. 20 parts by weight of compound no. 20 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

IV. 20 parts by weight of compound no. 19 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 80 parts by weight of compound no. 22 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

VI. 5 parts by weight of compound no. 3 is intimately mixed with 95 parts by weight of particulate kaolin. A dust is obtained containing 5% by weight of the active ingredient.

VII. 30 parts by weight of compound no. 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 3 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The agents may be applied pre- or postemergence. Preferably, the novel active ingredients, or agents containing them, are applied after emergence of the unwanted plants. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the plants to be combated, and the growth stage of the plants, and varies from 0.025 to 5 kg/ha and more, but is preferably from 0.125 to 3 kg/ha.

The influence of cyclohexane-1,3-dione derivatives of the formula I on the growth of grasses (Gramineae) and broadleaved crop plants is demonstrated in greenhouse experiments.

The vessels employed were plastic flowerpots having a volume of 300 cm$^3$, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate was 3.0 kg of active ingredient per hectare. After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. The soybean plants used for the postemergence treatment were grown in a peat-enriched substrate to ensure better growth than is possible in a sandy loam. For this treatment, either plants which had been sown directly in the pots and grown there were selected, or plants which had been grown separately as seedlings and transplanted to the experiment vessels a few days before treatment. No covers were placed on the pots in this treatment method. The application rates for postemergence treatment varied from ingredient to ingredient, and were either 0.125 or 0.25 kg of active ingredient per hectare.

The pots were set up in the greenhouse-species from warmer areas at from 20° to 35° C., and species from moderate climates at 10° to 20° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The following test plants were used in the experiments:
*Alopecurus myosuroides* (slender foxtail)
*Beta vulgaris* (sugarbeets)
*Brassica napus* (rapeseed)
*Bromus tectorum* (downy brome)
*Digitaria sanguinalis* (large crabgrass)
*Echinochloa crus-galli* (barnyardgrass)
*Glycine max.* (soybeans)
*Lolium multiflorum* (Italian ryegrass)
*Setaria italica* (foxtail)
*Triticum aestivum* (wheat).

The agent used for comparison purposes was 2-(1-ethoxyaminobutylidene)-5-(2-ethylthiopropyl)- cyclohexane-1,3-dione (German Laid-Open Application DE-OS No. 2,822,304)-A.

On preemergence application, for example compound nos. 1, 3, 16, 17, 19 and 20 had a marked herbicidal action on grassy species.

On postemergence application, for example compound no. 22, applied at rates of 0.125 and 0.25 kg/ha, combated unwanted plant species, and was fully tolerated by broadleaved crop plants and impaired wheat only slightly. By contrast, prior art comparative agent A caused very heavy damage to wheat. Compound no. 3, on postemergence application, had a better action on Bromus tectorum than comparative agent A.

In view of the good tolerance of the compounds according to the invention and the numerous application methods possible, they may be used in a further large number of crops for removing unwanted grasses, or grassy crop plants growing where they are not required.

The following crops may be mentioned by way of example:

| Botanical name | Common name |
|---|---|
| Allium cepa | onions |
| Ananas comosus | pineapples |
| Arachis hypogaea | peanuts (groundnuts) |
| Asparagus officinalis | asparagus |
| Beta vulgaris spp. altissima | sugarbeets |
| Beta vulgaris spp. rapa | fodder beets |
| Beta vulgaris spp. esculenta | table beets, red beets |
| Brassica napus var. napus | rape |
| Brassica napus var. napobrassica | |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Phaseolus lunatus | limabeans |
| Phaseolus mungo | mungbeans |
| Phaseolus vulgaris | snapbeans, green beans, dry beans |
| Petroselinum crispum | parsley |
| spp. tuberosum | |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |

To increase the spectrum of action and to achieve synergistic effects, the cyclohexane-1,3-dione derivatives of the formula I may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenyl-carbamates, thiolcarbamates, halocarboxylic acids, triazines, amides, ureas, diphenyl ethers, triazinones, uracils, benzofuran derivatives, etc.

It may also be useful to apply the novel compounds, either on their own or combined with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

We claim:

1. A cyclohexane-1,3-dione derivative of the formula

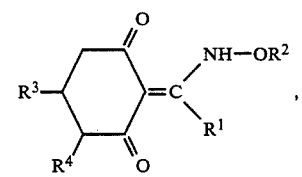

where $R^1$ is $C_1$–$C_4$-alkyl, $R^2$ is $C_1$–$C_5$-alkyl, unsubstituted or halogen-substituted $C_2$–$C_5$-alkenyl or $C_2$–$C_5$-alkynyl, $R^3$ is $C_1$–$C_{10}$-alkyl, which contains 2, 3 or 4 of the hetero-atoms O and/or S and/or the groups —SO— and/or —$SO_2$— in any desired position and $R^4$ is hydrogen, cyano, methyl or —$COOR^5$, where $R^5$ is $C_1$–$C_5$-alkyl, or a salt thereof.

2. A cyclohexane-1,3-dione of the formula I as claimed in claim 1, where $R^3$ is alkylthioalkylthioalkyl or alkoxyalkoxyalkyl of 3 to 10 carbon atoms and $R^4$ is hydrogen.

3. 2-(1-Ethoxyaminobutylidene)-5-(2-ethylthioethylthio-n-propyl)-cyclohexane-1,3-dione.

4. A herbidical composition for use on unwanted grasses which comprises: inert additives and from 0.1 to 95 wt% of a cyclohexane-1,3-dione derivative of the formula I or a salt of such a cyclohexane-1,3-dione derivative as claimed in claim 1.

5. A herbicidal composition as defined in claim 4, where $R^3$ of the compound of the formula I is alkylthioalkylthioalkyl or alkoxyalkoxyalkyl of 3 to 10 carbon atoms and $R^4$ is hydrogen, or a salt of such a cyclohexane-1,3-dione derivative.

6. A herbicidal composition for use on unwanted grasses comprising: inert additives and from 0.1 to 95 wt% of 2-(1-ethoxyet hoxyaminobutylidene)-5-(2-ethylthioethylthio-n-propyl)-cylclohexane-1,3-dione.

7. A process for combating the growth of unwanted grasses, wherein the unwanted grasses and/or the area to be kept free from the unwanted grasses are treated with a herbicidally effective amount of a cyclohexane-1,3-dione derivative of the formula I as claimed in claim 1, or a salt of a cyclohexane-1,3-dione derivative of the formula I as claimed in claim 1.

* * * * *

UNITED STATES PATENT AND TRADEMARK OFFICE
CERTIFICATE OF CORRECTION

PATENT NO.   : 4,517,013

DATED        : May 14, 1985

INVENTOR(S)  : Rainer BECKER et al.

It is certified that error appears in the above-identified patent and that said Letters Patent is hereby corrected as shown below:

ON THE COVER SHEET

Please insert the following:

[30]     Foreign Application Priority Data

July 24, 1982 Fed. Rep. of Germany......3227332

Signed and Sealed this

Fourteenth Day of January 1986

[SEAL]

Attest:

Attesting Officer

DONALD J. QUIGG

Commissioner of Patents and Trademarks